United States Patent [19]

Knollmueller

[11] 4,329,485

[45] May 11, 1982

[54] PROCESS FOR PREPARING ALKOXYSILANE CLUSTER COMPOUNDS BY REACTING A TRIALKOXYSILANOL WITH A TRIAMIDOSILANE

[75] Inventor: Karl O. Knollmueller, Hamden, Conn.

[73] Assignee: Olin Corporation, New Haven, Conn.

[21] Appl. No.: 278,149

[22] Filed: Jun. 29, 1981

[51] Int. Cl.³ .......................... C07F 7/18; C07F 7/08; C07F 7/04
[52] U.S. Cl. ..................................... 556/458; 556/451
[58] Field of Search ................................ 556/451, 458

[56] References Cited

U.S. PATENT DOCUMENTS

| 2,758,126 | 8/1956 | Goldschmidt et al. | 260/448.8 |
|---|---|---|---|
| 2,758,127 | 8/1956 | Goldschmidt et al. | 260/448.8 |
| 3,965,135 | 6/1976 | Knollmueller | 556/458 |
| 3,965,136 | 6/1976 | Knollmueller | 260/448.8 A |
| 4,077,993 | 3/1978 | Knollmueller | 260/448.8 R |
| 4,175,049 | 11/1979 | Knollmueller | 556/451 X |

OTHER PUBLICATIONS

J. R. Wright et al., "Silicate Esters and Related Compounds. I. Synthesis of Certain Tetraalkoxysilanes, Polyalkoxysiloxanes, Bis-(trialkoxysilyl)-alkanes and Related Intermediates", *Journal of the American Chemical Society*, vol. 80, pp. 1733–1737 (Apr. 5, 1958).

C. R. Morgan et al., "Synthesis of Alkoxy Silanols and Siloxanes", *Journal of the American Chemical Society*, vol. 73, pp. 5193 and 5195, Nov. 1951.

Herbert H. Anderson, "Methylanilinosilanes and Ethylanilinosilanes; Reactions of Anilinosilanes", *Journal of the American Chemical Society*, vol. 73, pp. 5802 and 5803, Dec. 1951.

Herbert H. Anderson, "Dialkylaminogermanes and Dialkylaminosilanes", *Journal of the American Chemical Society*, vol. 74, pp. 1421–1423, Mar. 20, 1952.

Robert N. Scott et al., "Silicate Cluster Fluids", I&EC Product Research & Development, vol. 19, Mar. 1980, pp. 6–11.

Olin Corporation Product Bulletin for Silicate Cluster ™ 102 Functional Fluid–Physical and Chemical Properties.

A Brief Synopsis of Olin Corporation's U.S. Patents Relating to Silicate Cluster ™ Shielded Polysilicate Compounds and Methods of Their Preparation & Use.

*Primary Examiner*—Paul F. Shaver
*Attorney, Agent, or Firm*—William A. Simons; Thomas P. O'Day

[57] ABSTRACT

Described is a process for producing alkoxysilane cluster compounds by reacting a trialkoxysilanol with a triamidosilane; this reaction being based on the following equation:

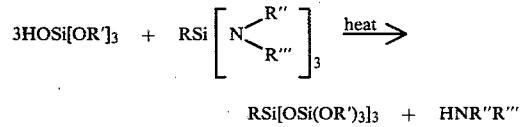

wherein R is hydrogen, an alkyl, an alkenyl, an aryl, or an aralkyl; each R' is independently selected from the same groups as R with the proviso that at least a majority of said R' radicals are sterically hindered alkyl groups having at least 3 carbon atoms; and R" and R'" are individually selected from hydrogen, lower alkyl groups having 1–4 carbon atoms, and phenyl with the proviso that both R" and R'" may not be hydrogen.

9 Claims, No Drawings

PROCESS FOR PREPARING ALKOXYSILANE CLUSTER COMPOUNDS BY REACTING A TRIALKOXYSILANOL WITH A TRIAMIDOSILANE

BACKGROUND OF THE INVENTION

1. Field of the Invention

This invention relates to a process for producing alkoxysilane cluster compounds.

2. Description of the Prior Art

U.S. Pat. No. 3,965,136, which issued to the present inventor on June 22, 1976, disclosed the preparation of alkoxysilane cluster compounds of the formula:

RSi[OSi(OR')$_3$]$_3$     (I)

wherein R is hydrogen, an alkyl, alkenyl, aryl, or aralkyl; and each R' is independently selected from the same groups as R with the proviso that at least a majority of the R' radicals are sterically hindered alkyl groups having at least 3 carbon atoms. These alkoxysilane compounds of formula (I) have been disclosed to be good functional fluids because of their unique combination of properties. Potential applications include high performance hydraulics, heat transfer agents, greases, dielectric coolants, and as a formulating aid in combination with other fluids.

In particular, two different processes for preparing these alkoxysilane cluster compounds are disclosed in U.S. Pat. No. 3,965,136. The first method of preparation involves the reaction of a trihalosilane with a trialkoxysilanol in the presence of an acid acceptor like pyridine. The second disclosed method of preparation involves the reaction of halosilane with an alkoxysilanol cluster compound in the presence of an acid acceptor.

An optimization of the above-noted first method of preparation is disclosed in U.S. Pat. No. 4,077,993, which also issued to the present inventor on Mar. 7, 1978. This improved method of preparation involves reacting a trihalosilane with a trialkoxysilanol in the presence of critical amounts of acceptor base and solvent reaction medium while maintaining the reaction temperature in a select range.

It has been found that these two methods for preparing alkoxysilane cluster compounds of formula (I) are somewhat hindered by the fact that they require an acid acceptor. Suitable acid acceptors such as pyridine are relatively expensive and must be recovered from the reaction mixture in order to reduce the cost of the synthesis. However, the recovery steps themselves are expensive to run on a large scale. Also, the yield of the alkoxysilane cluster product may be reduced because the occlusion of some of the product to the acid acceptor salt, even after washing steps. Furthermore, organic acid acceptors such as pyridine and the like have unpleasant physical characteristics and their use may present a health hazard in some circumstances.

Furthermore, it has been found that the use of certain trihalosilane intermediates does not result in desirably high yields of alkoxysilane cluster compounds for commerical use. The exact reasons for this is not known, but most likely involves steric hindrance of the reaction transition complexes of reactants and acid acceptor.

For the above and other reasons, a method for preparing alkoxysilane cluster compounds is needed which is relatively inexpensive and which does not require the use of pyridine or any other type of acid acceptor compound. The present invention, as described in detail below, presents a solution to this need.

Separately, polyalkoxy di-, tri-, and tetrasiloxanes have been prepared by reacting the corresponding alkoxysilanol with an appropriate alkoxysilamine. See U.S. Pat. No. 2,758,127, which issued to Goldschmidt et al on Aug. 7, 1956. However, this disclosed reaction was directed toward making linear-structured siloxanes, and not branched-structured compounds having sterically hindered alkoxy groups as is the present case.

BRIEF SUMMARY OF THE INVENTION

Therefore, the present invention is directed to a process for preparing an alkoxysilane cluster compound of the formula (I):

RSi[OSi(OR')$_3$]$_3$     (I)

wherein R is hydrogen, alkyl, alkenyl, aryl, or aralkyl; each R' is independently selected from the same groups as R with the proviso that at least a majority of said R' radicals are sterically hindered alkyl groups having at least 3 carbon atoms, comprising reacting a trialkoxysilanol of the formula (II):

HOSi[OR']$_3$     (II)

wherein R' is defined above, with a triamidosilane of the formula (III):

(III)

wherein R is defined above, and R" and R'" are individually selected from hydrogen, lower alkyl groups having 1-4 carbon atoms and phenyl with the proviso that both R" and R'" may not be hydrogen;

employing at least 2.5 moles of the trialkoxysilanol per one mole of the triamidosilane;

and the reaction being carried out at about 60° C. to about 200° C.

DETAILED DESCRIPTION

The improved method for preparing alkoxysilane cluster compounds of formula (I) involves the reaction outlined in Equation (A) below between a trialkoxysilanol and a triamidosilane.

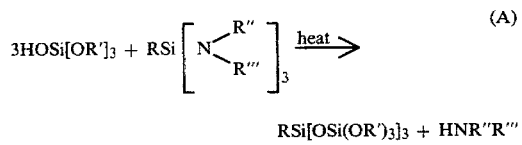

(A)

wherein R, R', R" and R'" are as defined above.

The trialkoxysilanol reactants [represented by formula (II), above] and the methods of their preparation are disclosed in U.S. Pat. Nos. 4,198,346 and 4,207,247, both of which issued to the present inventor on Apr. 15, 1980, and June 10, 1980, respectively. The disclosures of these two U.S. Patents are incorporated herein by reference in their entirety. However, these trialkoxysilanol reactants may be made by other known methods and the present invention is not to be limited to any such method of their preparation.

The preferred examples of these trialkoxysilanol reactants have R' radicals which are individually selected from hydrogen, alkyl or alkenyl groups having from 1 to about 18 carbon atoms, or aryl or aralkyl groups having about 6 to about 24 carbon atoms, subject to the proviso that at least a majority of the R' radicals are sterically hindered alkyl groups having 3 to about 18 carbon atoms. More preferably, all of the R' radicals of this reactant are sterically hindered alkyl groups having about 4 to about 12 carbon atoms. Most preferably, all of the R' radicals are sterically hindered alkyl groups derived from secondary or tertiary alcohols and having about 4 to about 12 carbon atoms. A specific example of the most preferred R' radical is a sec-butyl group.

Sterically hindered alkyl groups are defined as alkyl radicals which contribute to the hydrolytic stability of the molecule, i.e., which inhibit the reaction of water with silicon-oxygen or the carbon-oxygen bonds in the molecule. Exemplary of preferred sterically hindered alkyl R' radicals include (1) non-linear primary alkyl radicals having a beta position side chain of at least 2 carbons, (2) secondary alkyl radicals, and (3) tertiary alkyl radicals. However, it has now been found that cluster products of the present invention containing the R' radicals of the latter two classes (e.g., secondary alkyl groups such as sec-butyl and the like, and tertiary alkyl groups such as tert-butyl, 1,1-dimethylpropyl, 1,1-dimethylallyl and the like) are somewhat easier to prepare than cluster compounds of this invention containing the non-linear primary alkyl radicals (e.g., isobutyl, 2-ethyl butyl, 2-ethyl pentyl, 3-ethyl pentyl, 2-ethyl hexyl, 2,4-dimethyl-3-pentyl, and the like).

Representative trialkoxysilanol reactants for the method of the present invention include those named in the following Table (I):

TABLE I

REPRESENTATIVE TRIALKOXYSILANOLS

| Name | Chemical Formula |
|---|---|
| tri-isopropoxysilanol | $[C_3H_7O]_3SiOH$ |
| tri-sec-butoxysilanol | $[sec-C_4H_9O]_3SiOH$ |
| tri-tert-butoxysilanol | $[tert-C_4H_9O]_3SiOH$ |
| di-(tert-butoxy) (sec-butoxy)silanol | $[tert-C_4H_9O]_2[sec-C_4H_9O]SiOH$ |
| di(sec-butoxy) (isopropoxy)silanol | $[sec-C_4H_9O]_2[C_3H_7O]SiOH$ |
| tri(3-pentaneoxy)silanol | $[(CH_3CH_2)_2CHO]_3SiOH$ |
| tri-2-ethylhexoxysilanol | $[C_8H_{17}O]_3SiOH$ |
| tri-2-ethylbutoxysilanol | $[C_6H_{13}O]_3SiOH$ |
| di(sec-butoxy) (2-ethylhexoxy)silanol | $[sec-C_4H_9O]_2[C_8H_{17}O]SiOH$ |
| di(sec-butoxy) (1,1-dimethylallyloxy)silanol | $[sec-C_4H_9O]_2[H_2C=CH(CH_3)_2CO]SiOH$ |
| di(tert-butoxy) (allyloxy)silanol | $[tert-C_4H_9O]_2CH_2=CHCH_2O]SiOH$ |
| tri-phenoxysilanol | $[C_6H_5O]_3SiOH$ |
| tri-(octylphenoxy)silanol | $[C_{14}H_{21}O]_3SiOH$ |

Some triamidosilane reactants of the present invention [represented by formula (III), above] and the methods of their preparation are disclosed by H. Anderson in the *Journal of the American Chemical Society*, Vol. 73, page 4802 (1951) and Vol. 74, page 1421 (1952). Other triamidosilanes of the present invention may be made by analogous methods or by other conventional procedures. The disclosures of these two articles by H. Anderson are incorporated herein by reference in their entirety.

In preferred embodiments of the present invention, the R radical on these triamidosilane reactants includes either hydrogen, an alkyl or an alkenyl having 1 to 24 carbon atoms, or an aryl or an aralkyl having from about 6 to about 24 carbon atoms. More preferably, R is either hydrogen, an alkyl or alkenyl group having 1 to about 8 carbon atoms, or an aryl or aralkyl having about 6 to about 14 carbon atoms. Most preferably, R is either hydrogen or a lower alkyl group having 1 to 4 carbon atoms.

As stated above, the radicals R'' and R''' on the triamidosilane reactant are individually selected from hydrogen, lower alkyl groups having 1–4 carbon atoms, and phenyl groups with the proviso that both R'' and R''' may not be hydrogen. In preferred embodiments, R'' and R''' are selected from either hydrogen, or a lower alkyl having 1 to 4 carbon atoms, subject to the same proviso. More preferably, R'' and R''' are the same lower alkyl group having 1 to 4 carbon atoms. Most preferably, both R'' and R''' are methyl since dimethylamine will be formed as a co-product with the desired alkoxysilane cluster product (I). Dimethylamine is a preferred co-product since it is volatile, and thus easy to remove from the desired cluster product. The radicals R'' and R''' may not both be hydrogen because undesirable self-condensation reactions may occur which could prevent the formation of the wanted alkoxysilane cluster products (I).

Representative triamidosilane reactants for the method of the present invention include those named in the following Table (II):

TABLE II

REPRESENTATIVE TRIAMIDOSILANES

| Name | Chemical Formula |
|---|---|
| tris-N,N-dimethylamidosilane | $[(H_3C)_2N]_3SiH$ |
| tris-N,N-dimethylamidomethylsilane | $[(H_3C)_2N]_3SiCH_3$ |
| tris-N,N-dimethylamidophenylsilane | $[(H_3C)_2N]_3SiC_6H_5$ |
| tris-N,N-dimethylamidotolylsilane (ortho,meta, or para) | $[(H_3C)_2N]_3SiC_7H_7$ |
| tris-N,N-dimethylamido-n-hexylsilane | $[(H_3C)_2N]_3Si-C_6H_{13}$ |
| tris-N,N-dimethylamidooctylsilane | $[(H_3C)_2N]_3SiC_8H_{17}$ |
| tris-N,N-dimethylamidovinylsilane | $[(H_3C)_2N]_3SiCH=CH_2$ |
| tris-N,N-dimethylamidoallylsilane | $[(H_3C)_2N]_3SiCH_2CH=CH_2$ |
| tris-N,N-diethylamidosilane | $[(C_2H_5)_2N]_3SiH$ |
| tris-N,N-diethylamidomethylsilane | $[(C_2H_5)_2N]_3SiCH_3$ |
| tris-anilido-silane | $[C_6H_5NH]_3SiH$ |
| tris-anilido-methylsilane | $[C_6H_5NH]_3SiCH_3$ |
| tris-anilido-phenylsilane | $[C_6H_5NH]_3SiC_6H_5$ |
| tris-anilido-tolysilane (ortho, meta, or para) | $[C_6H_5NH]_3SiC_7H_7$ |
| tris-anilido-vinylsilane | $[C_6H_5NH]_3SiCH=CH_2$ |

The mole ratio of the trialkoxysilanol to the triamidosilane as reactants should be at least about 2.5:1 to ensure a desired yield of the alkoxysilane cluster product. Preferably, this mole ratio is in the range of about 2.9:1 to about 3.3:1. Most preferably, this mole ratio is in the range of about 2.95:1 to about 3.05:1.

Suitable temperatures for this type of reaction are generally in the range from about 60° C. to about 200° C. with the preferred range from about 100° C. to about 190° C. and the most preferred range of reaction temperatures from about 130° C. to about 170° C. Of course, the specific temperature preference will depend upon the particular reactants employed. Lower reaction temperatures will usually be employed with relatively more volatile reactants and temperatures may be needed to be increased after the reaction has begun.

The reaction may be carried out in the absence of any above-atmospheric pressure. Sub-atmospheric pressure may be employed to remove any volatile amino co-product and to drive the reaction faster. The reaction is preferably carried out at atmospheric pressure or below that pressure (e.g. from about 760 mm Hg to about 300 mm Hg).

The time of the reaction will depend upon many factors including the reaction temperature and specific reactants employed. Generally, reaction times may vary from about 30 minutes to about 200 minutes or more. However, the present invention is not to be limited to any particular range of reaction times.

Reaction of Equation (A) above may, in some instances, be carried out in the presence of a solvent, but one is not necessary. A solvent may serve to moderate the rate of reaction. Any solvent may be used which dissolves the reactants and does not interfere with reaction of Equation (A).

Once the reaction is substantially complete, as evidenced by a reduction or cessation of the amine evolution, the reaction may be terminated and the alkoxysilane cluster product recovered, preferably by fractional distillation under reduced pressures. Furthermore, the recovered cluster product may be water washed or subjected to other conventional purification techniques besides being distilled.

As stated above, the products of this inventive process are disclosed in U.S. Pat. No. 3,965,136 as having properties which are especially good for functional fluid systems or other applications.

The process of the present invention is illustrated by the following examples. All parts and percentages are by weight unless explicitly stated otherwise.

EXAMPLE 1

PREPARATION OF $H_3C\ Si[OSi(OC_4H_9sec)_3]_3$

The experimental set-up was typical for all experiments and the procedure is therefore described fully in this example. Variations were in equipment size to accommodate large batches. A 100 ml three-necked flask was equipped with a magnetic stirring bar, a thermometer, a gas inlet tube and a small reflux condenser. The exit of the reflux condenser was attached to a downward fritte. The fritte dipped into a Erlenmeyer flask containing 200 ml water and a drop methyl red indicator. The reaction flask was charged with 13.6 g tris N,N-dimethylamido methylsilane of the formula $H_3C\text{-}Si[N(CH_3)_2]_3$. This was 0.078 mole. To it was added 67.2 g silanol of the formula $(sC_4H_9O)_3SiOH$ or 0.234 moles. A slow stream of $N_2$ was passed through the system to pass the liberated dimethylamine into the absorber. The contents of the flask were now heated in an oil bath. The reaction started at 90° C. but became noticably fast at about 110°. The dimethylamine liberated was titrated with 1 N HCl and the progress of the reaction thus followed. During the run the temperature was allowed to rise to 160°. When no more dimethylamine came off, the temperature was briefly raised to 190° C. Thus monitoring the dimethylamine release we found that between 120° and 150° two moles (per mole amide charged) were released within 20 minutes, while the last mole amine came off in about 40 minutes more. 68 g crude product was thus obtained assaying 70% cluster and 18% high boiler. This represented a 73.2% yield.

To purify the cluster and free it from traces of compounds having SiN bonds, the crude material was dissolved in 150 ml toluene in order to reduce the density and facilitate easy water washes. This solution was stirred overnight with 20 ml water. The organic phase was phased, washed once with diluted HCl (20 ml) (to give a pH of 3-4) followed by a wash with 100 ml saturated $NaHCO_3$ solution and 3 water washes. The organic phase was now dried over $MgSO_4$ filtered and the solvent vacuum stripped. Distillation on a micro Vigreux column gave a forecut containing low boilers and 37 g product boiling at 192°/0.05 mm Hg.

The physical properties of the product were identical to the same products prepared by the synthesis disclosed in U.S. Pat. Nos. 3,965,136 and 4,077,993.

EXAMPLE 2

PREPARATION OF $H_3C\text{-}Si[OSi(OC_4H_9sec)_2OC(CH_3)_2CH=CH_2]_3$

This example demonstrates the synthesis of a cluster containing three sterically hindered tertiary alkenyl groups.

Into the apparatus described in Example 1 were weighed the following components:

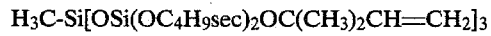
$H_3C\text{-}Si[N(CH_3)_2]_3 [2.27\ g (0.0414\ mole)]$

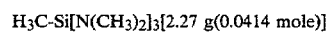
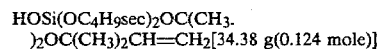
$HOSi(OC_4H_9sec)_2OC(CH_3\text{-})_2OC(CH_3)_2CH=CH_2 [34.38\ g (0.124\ mole)]$ Heating these components within 17 minutes to 157° C. released 70% of the theoretically possible dimethylamine. Within 70 minutes at 160° C. the theoretical amount of dimethylamine was expelled. After the usual hydrolysis/wash work-up there was obtained 37 g material, assaying at 94.4% by VPC. This is 0.0402 mole or 96.9% yield.

Distillation on micro equipment showed a boiling point of 204°/0.2 mm. Since a residue formed on distillation, a larger batch prepared similarily was purified by molecular distillation. At 200° to 220° evaporator temperature and $10^{-4}$ mm Hg in a wiped film molecular still the cluster distilled to 98% purity by VPC Analysis. The yield after distillation was 92%. Refractive Index $n_D^{20}=1.4295$.

Analysis for $Si_4C_{40}H_{84}O_{12}$ (MW 869.444).

Calculated:
 Si—12.92%,
 C—55.26%
 H—9.74%.

Found:
 Si—12.19, 12.68%,
 C—54.91, 54.99%,
 H—9.52, 9.68%.

EXAMPLE 3

LARGER SCALE PREPARATION OF $H_3C-Si[OSi(OC_4H_9sec)_2OC(CH_3)_2CH=CH_2]_3$

This is an improvement of Example 2 and shows that the reaction may be carried out at lower temperatures over a longer period of time. Following the procedures outlined in Example 1, but reacting a mixture of 299.4 g $HOSi(OC_4H_9sec)_2(OC(CH_3)_2CH=CH_2)$ (assay 96.7% = 1.049 mole) and 62.0 g $H_3C-Si[N(CH_3)_2]_3$, (assay 98.9% = 0.3497 mole) for 19 hours at 110° C. gave 303.0 g of crude cluster compound assaying 90.6%. This represented a yield of 90.3% crude material. The product was vacuum fractionated through a Vigreux column. After taking forecuts assaying up to 98% (weight 36 g), the main product distilled at 189°-192° C. at 0.07 mm Hg (weight 191 g and 98.2% purity). An aftercut weighed 21.5 g but showed 95.5% purity and the remaining condensed material weighed 54.3 g. The main material was 0.219 mole which is an in-hand yield of 62.8%.

The properties of the product were identical to the ones prepared in Example 2.

EXAMPLE 4

PREPARATION OF $H_2C=CHSi[OSi(OC_4H_9sec)_2OC(CH_3)_2CH=CH_2]_3$

Following the procedure outlined in Example 1, but reacting a mixture of 21.8 g $HOSi(OC_4H_9sec)_2OC(CH_3)_2CH=CH_2$ (assay 98% by VPC = 0.077 mole) and 4.83 g $H_2C=CHSi[N(CH_3)_2]_3 = 0.026$ moles to 140° C. released 87% of the amine in 30 minutes and the remainder within one hour.

After work-up there was obtained 21.7 g of cluster showing a VPC purity of 90.3%. This represents a VPC yield of 86.3%. The refractive index was 1.4339.

Analysis for $Si_4C_{41}H_{84}O_{12}$ (MW 881.455)
Calculated:
  Si—12.74%,
  C—55.87%,
  H—9.61%.
Found:
  Si—12.92%,
  C—55.92; 55.90%,
  H—9.78; 9.84%.

EXAMPLE 5

LARGE SCALE PREPARATION OF $H_2C=CHSi[OSi(OC_4H_9sec)_2OC(CH_3)_2CH=CH_2]_3$ Repeating the experiment of Example 4 on a larger scale and reacting 87.76 g $HOSi(OC_4H_9sec)_2OC(CH_3)_2CH=CH_2$ [assay 98.7% (0.313 mole)] and 19.96 g $H_2C=CHSi[N(CH_3)_2]_3$ [assay 99% (0.1044 mole] for 3 hours at 130°-142° C. gave 89.7 g crude cluster compound of an assay of 87.6% by VPC, which represents an 85.4% yield. Without going through the wash procedure the product was fractionated in a micro Vigreux column. The fraction collected at 191°-194° C./0.07 mm Hg had a purity of 97.1% and weighed 55.48 g, which is a 58.5% in-hand yield.

EXAMPLE 6

PREPARATION OF $H_2C=CH-Si[OSi(OC_4H_9sec)_2(OC_4H_9tert)]_3$

This example demonstrates the synthesis of a cluster containing secondary and tertiary alkoxy groups and an unsaturated alkyl group on the central silicon atom.

Into the apparatus described in Example 1 was charged 15.81 g tris-N,N-dimethylamido vinyl silane of the formula $H_2C=CH-Si[N(CH_3)_2]_3$ (0.084 mole) and 66.7 g di sec butoxy-tert butoxy-silanol of the formula $HOSi(OC_4H_9sec)_2(OC_4H_9tert)$ (0.252 mole).

Within one and one-half hours at temperatures between 140°-167° C. the dimethylamine was liberated. After work-up, 70 g of crude product with an assay of 91.5% was obtained.

The product was distilled on a Vigreux column to >97% purity bp 201° at 0.05 mm Hg. During the distillation the condenser had to be above 50° C. since the product crystallized.

The yield after distillation was 73.3% mp 52.5° C. Analysis for $Si_4C_{38}H_{84}O_{12}$ (MW 845.422):
Calculated:
  Si—13.29%,
  C—53.94%,
  H—10.01%.
Found
  Si—13.2, 12.8%,
  C—53.8, 53.91%,
  H—9.8, 9.84%.

EXAMPLE 7

PREPARATION OF $H_3C-Si[OSi(OC_4H_9sec)_2(OC_4H_9tert)]_3$

This example demonstrates the synthesis of a cluster containing secondary and tertiary alkoxy groups.

Into the apparatus described in Example 1 was weighed 4.44 g tris-N,N-dimethylamido methylsilane of the formula $H_3C-Si[N(CH_3)_2]_3$ (0.025 moles) and 20.09 g di sec-butoxy-tert butoxy-silanol of the formula $HOSi(OC_4H_9sec)_2(OC_4H_9tert)$ (0.076 moles). Within 30 minutes at 145° C., 94% of the theoretically possible dimethylamine was expelled. The rest was liberated in an additional hour. There was obtained 21.25 g crude product, which assayed 91.6% product (by VPC).

It was distilled on a micro Vigreux column; boiling point 192°-194° C. at 0.05 mm Hg. The product had a melting point of +10° to +11° C. Refractive index was 1.4186. Density (25° C.) was 0.973. Its viscosity at 100° F. was 101.64 cst while at 210° F. the viscosity was 19.31 cst from which an ASTM viscosity index of 207.9 is calculated.

Analysis for $Si_4C_{37}H_{84}O_{12}$ (MW 833.411)
Calculated:
  Si—13.48%
  C—53.32%
  H—10.16%
Found:
  Si—12.65%,
  C—52.4, 52.45%,
  H—9.63, 9.74%.

What is claimed is:
1. A process for preparing an alkoxysilane cluster compound of the formula:

RSi[OSi(OR')$_3$]$_3$ wherein R is hydrogen, alkyl, alkenyl, aryl, aralkyl; each R' is independently selected from the same group as R subject to a first proviso that at least a majority of said R' radicals are sterically hindered alkyl groups having at least 3 carbon atoms;

comprising reacting a trialkoxysilanol of the formula:

HOSi[OR']3 wherein R' is defined above, with a triamidosilane of the formula:

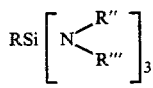

wherein R is defined above, and R" and R''' are individually selected from hydrogen, lower alkyl groups having 1–4 carbon atoms and phenyl, subject to a second proviso that both R" and R''' may not be hydrogen; employing at least 2.5 moles of said trialkoxysilanol per one mole of said triamidosilane;

and said reaction being carried out at about 60° C. to about 200° C.

2. The process of claim 1 wherein said R radical is either hydrogen, an alkyl or an alkenyl having 1 to 24 carbon atoms, or an aryl or an aralkyl having from about 6 to about 24 carbon atoms.

3. The process of claim 1 wherein said R' radicals are individually selected from hydrogen, alkyl or alkenyl groups having 1 to about 18 carbon atoms, or aryl or aralkyl groups having about 6 to about 24 carbon atoms, subject to said first proviso.

4. The process of claim 1 wherein said R" and R''' are selected from either hydrogen or a lower alkyl group from 1 to 4 carbon atoms, subject to said second proviso.

5. The process of claim 1 wherein said mole ratio of said trialkylsilanol to said triamidosilane is in the range of about 2.9:1 to about 3.3:1.

6. The process of claim 1 wherein said reaction temperature is in the range from about 100° C. to about 190° C.

7. The process of claim 1 wherein said R radical is either hydrogen, an alkenyl group having 1 to about 8 carbon atoms, or an aryl or aralkyl group having about 6 to about 14 carbon atoms and said R' radicals are all sterically hindered alkyl groups having 4 to about 12 carbon atoms.

8. The process of claim 7 wherein R" and R''' are the same lower alkyl group having 1 to 4 carbon atoms.

9. The process of claim 8 wherein R is methyl, the R' radicals are all sec-butyl, and R" and R''' are both methyl.

* * * * *